(12) United States Patent
Banet et al.

(10) Patent No.: US 8,506,480 B2
(45) Date of Patent: Aug. 13, 2013

(54) DEVICE FOR DETERMINING RESPIRATORY RATE AND OTHER VITAL SIGNS

(75) Inventors: Matthew J. Banet, Del Mar, CA (US); Zhou Zhou, San Diego, CA (US); Robert J. Kopotic, Jamul, CA (US); Marshal Singh Dhillon, San Diego, CA (US); Andrew Stanley Terry, San Diego, CA (US); Henk Visser, II, San Diego, CA (US)

(73) Assignee: Sotera Wireless, Inc., San Diego, CA (US)

( * ) Notice: Subject to any disclaimer, the term of this patent is extended or adjusted under 35 U.S.C. 154(b) by 1248 days.

(21) Appl. No.: 12/171,886

(22) Filed: Jul. 11, 2008

(65) Prior Publication Data

US 2009/0018409 A1 Jan. 15, 2009

Related U.S. Application Data

(60) Provisional application No. 60/949,052, filed on Jul. 11, 2007.

(51) Int. Cl.
*A61B 5/00* (2006.01)

(52) U.S. Cl.
USPC ........... 600/301; 600/300; 600/483; 600/484; 600/587

(58) Field of Classification Search
None
See application file for complete search history.

(56) References Cited

U.S. PATENT DOCUMENTS

| | | | |
|---|---|---|---|
| 5,022,402 A * | 6/1991 | Schieberl et al. | 600/484 |
| 5,309,922 A | 5/1994 | Schechter et al. | |
| 5,316,008 A | 5/1994 | Suga et al. | |
| 5,649,543 A | 7/1997 | Hosaka et al. | |
| 5,857,975 A | 1/1999 | Golub | |
| 5,865,755 A | 2/1999 | Golub | |
| 6,261,238 B1 | 7/2001 | Gavriely | |
| 6,375,621 B1 | 4/2002 | Sullivan | |
| 7,004,907 B2 | 2/2006 | Banet et al. | |
| 2004/0039295 A1 * | 2/2004 | Olbrich et al. | 600/538 |
| 2004/0077934 A1 * | 4/2004 | Massad | 600/300 |
| 2005/0124864 A1 | 6/2005 | Mack et al. | |
| 2005/0216199 A1 | 9/2005 | Banet | |
| 2005/0228296 A1 | 10/2005 | Banet | |

(Continued)

OTHER PUBLICATIONS

International Search Report and Written Opinion, International Patent Application No. PCT/US08/69862, mailed Oct. 22, 2008 (10 pages).

(Continued)

*Primary Examiner* — Bill Thomson
*Assistant Examiner* — Bobby Soriano
(74) *Attorney, Agent, or Firm* — Michael A. Whittaker; Acuity Law Group, PC

(57) ABSTRACT

A body-worn sensor that measures respiratory rate and other vital signs using an acoustic sensor (e.g., a small-scale sensor). The body-worn sensor features a chest-worn patch sensor that combines both the acoustic sensor and an ECG electrode into a single adhesive patch. To measure blood pressure, the device additionally performs a 'composite' PTT-based measurement that features both pressure-dependent and pressure-free measurements. The acoustic sensor measures respiration rate by recording sounds related to the patient's inspiration and expiration. The acoustic sensor is typically placed near the patient's trachea, but can also be placed on the middle right and left side of the chest, and the middle right and left side of the back.

20 Claims, 8 Drawing Sheets

(56) References Cited

U.S. PATENT DOCUMENTS

| | | |
|---|---|---|
| 2005/0228299 A1 | 10/2005 | Banet |
| 2005/0228300 A1 | 10/2005 | Jaime et al. |
| 2006/0009698 A1 | 1/2006 | Banet et al. |
| 2006/0220882 A1* | 10/2006 | Makino .................. 340/573.1 |
| 2006/0241510 A1 | 10/2006 | Halperin et al. |
| 2006/0264730 A1 | 11/2006 | Stivoric et al. |
| 2007/0142715 A1 | 6/2007 | Banet et al. |
| 2007/0185393 A1 | 8/2007 | Zhou et al. |
| 2007/0276261 A1 | 11/2007 | Banet et al. |
| 2007/0276632 A1 | 11/2007 | Banet et al. |
| 2007/0282212 A1* | 12/2007 | Sierra et al. .................. 600/529 |
| 2008/0004904 A1* | 1/2008 | Tran ................................ 705/2 |
| 2008/0082004 A1 | 4/2008 | Banet et al. |
| 2008/0091088 A1* | 4/2008 | Kiani ............................ 600/301 |
| 2008/0146890 A1* | 6/2008 | LeBoeuf et al. ............. 600/300 |
| 2008/0221399 A1 | 9/2008 | Zhou et al. |
| 2008/0306367 A1* | 12/2008 | Koehler et al. ............... 600/364 |
| 2009/0018422 A1 | 1/2009 | Banet et al. |
| 2009/0018453 A1 | 1/2009 | Banet et al. |
| 2009/0131759 A1* | 5/2009 | Sims et al. .................... 600/301 |
| 2009/0203972 A1* | 8/2009 | Heneghan et al. ............ 600/301 |

OTHER PUBLICATIONS

Leonard, et al., "A Fully Automated Algorithm for the Determination of Respiratory Rate from the Photoplethysmogram," Journal of Clinical Monitoring and Computing, 2006, 20:33-36, 4 pages.

Mazzanti, et al., "Validation of an ECG-Derived Respiration Monitoring Method," IEEE, Computers in Cardiology, 2003, 30:613-616, 4 pages.

Nakajima, et al., "Photoplethysmographic Measurement of Heart and Respiratory Rates Using Digital Filters," IEEE, 1/93, 1993, 2 pages.

* cited by examiner

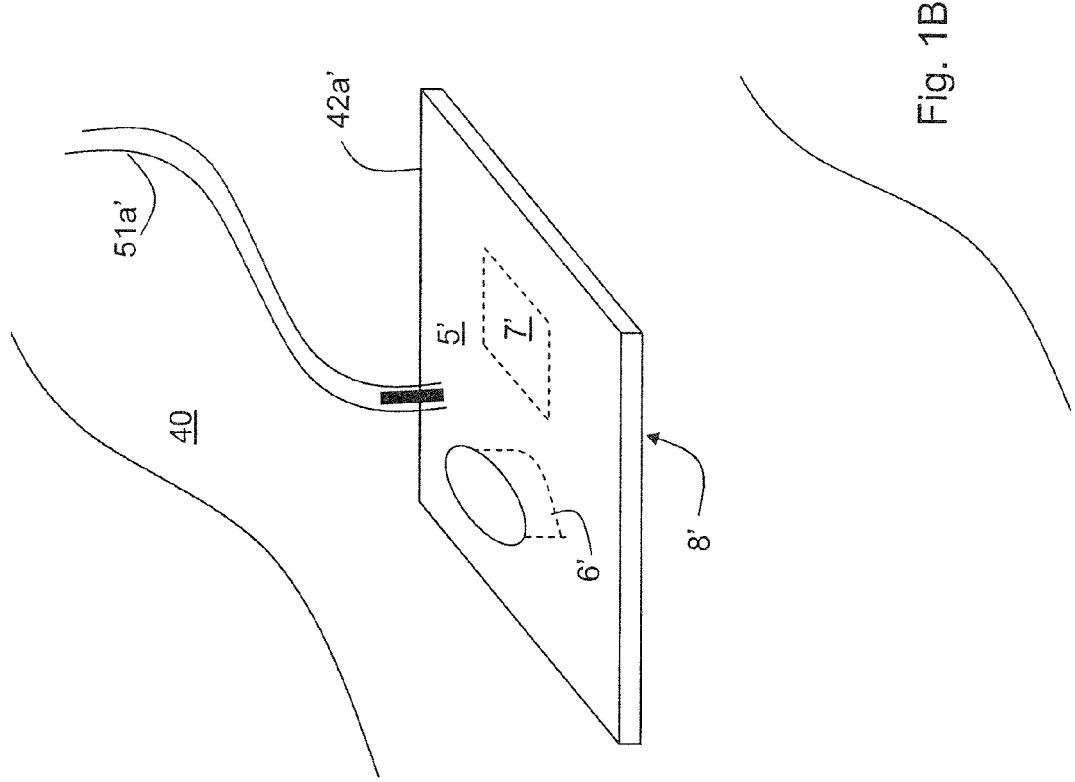
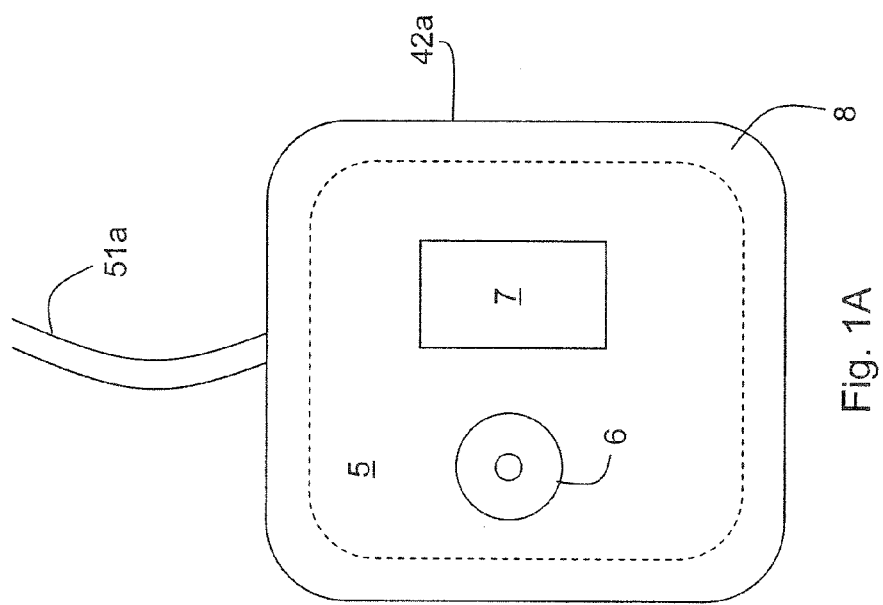

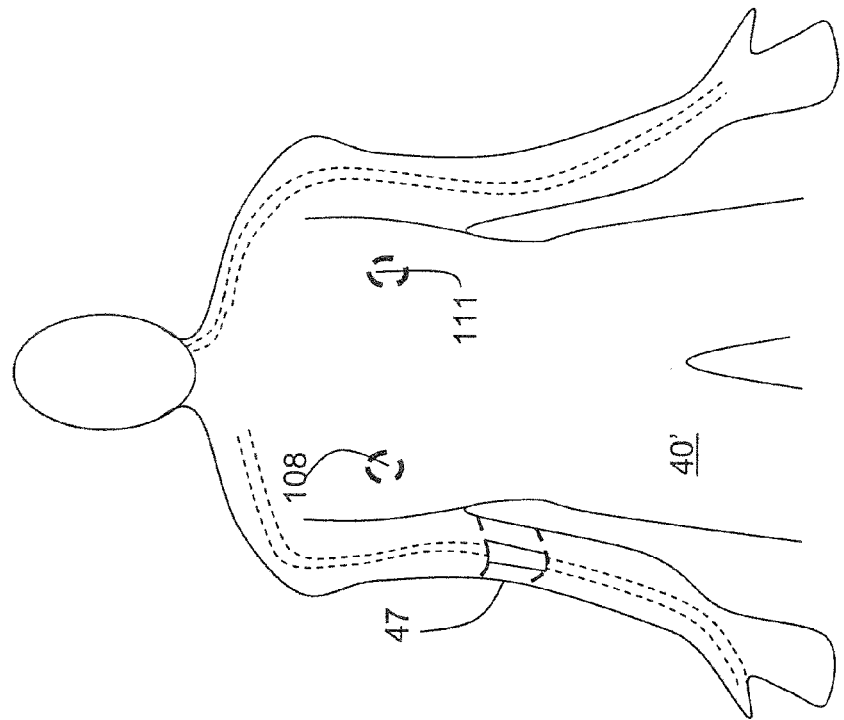
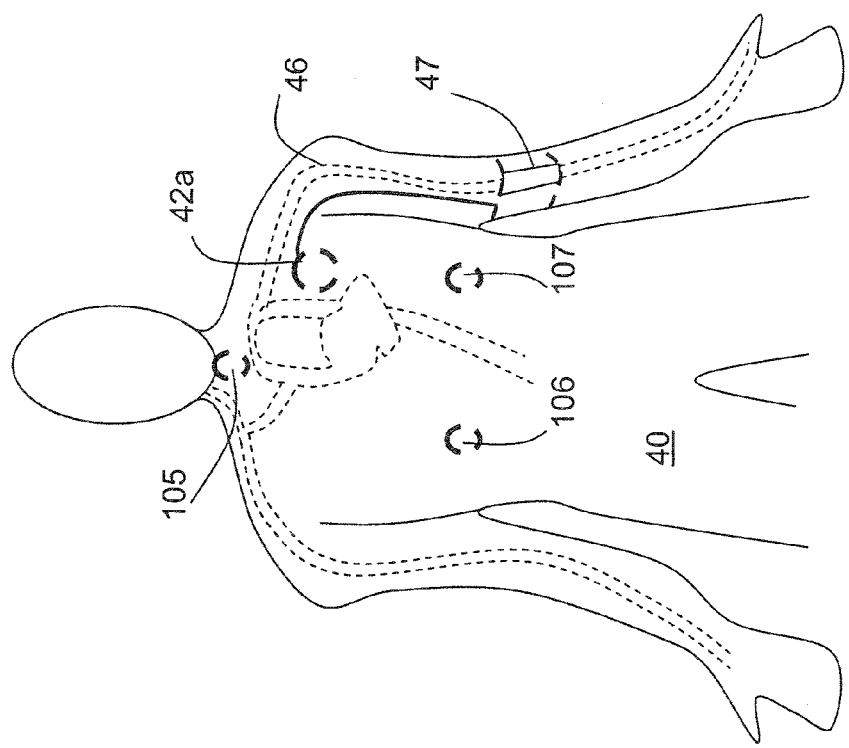
Fig. 5A  Front of Patient
Fig. 5B  Back of Patient

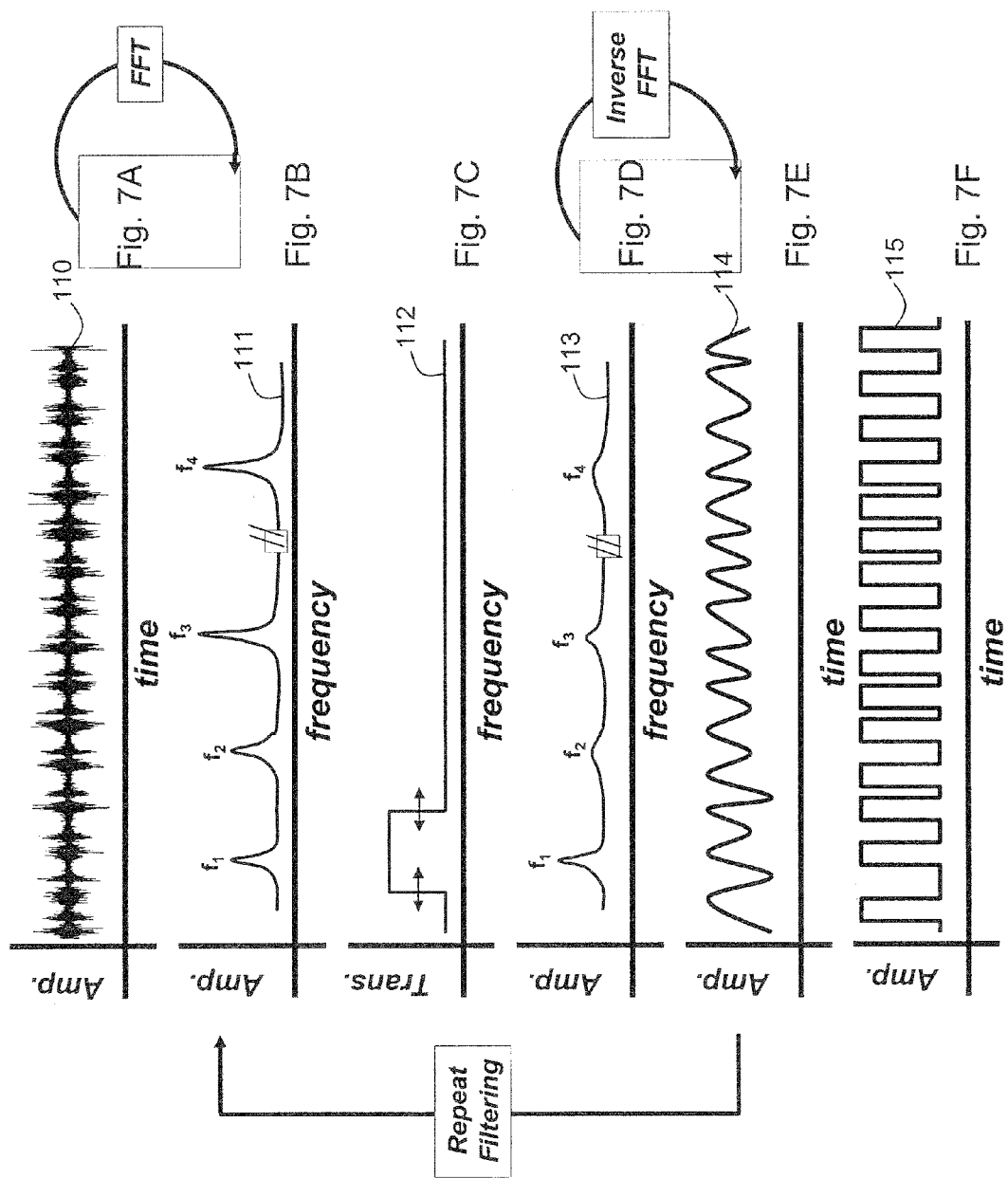

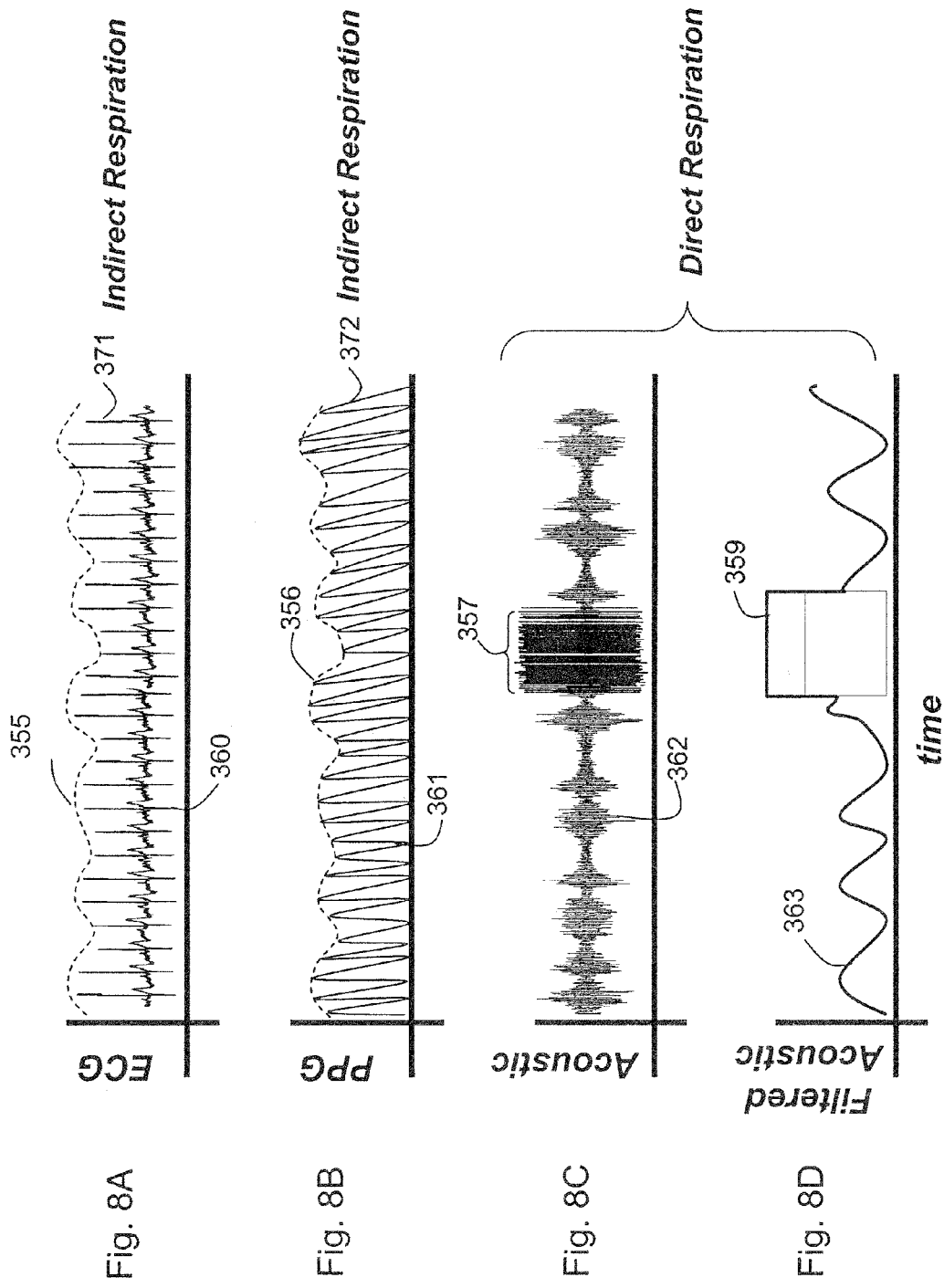

DEVICE FOR DETERMINING RESPIRATORY RATE AND OTHER VITAL SIGNS

This application claims the benefit of U.S. Provisional Application No. 60/949,052, filed Jul. 11, 2007, all of which is incorporated herein by reference.

FIELD OF THE INVENTION

This invention generally relates to medical devices for monitoring respiratory rate and other vital signs, e.g., blood pressure.

BACKGROUND OF THE INVENTION

Auscultation is defined as the act of listening for sounds made by a patient's internal organs (e.g., the heart and lungs) to aid in the diagnosis of certain disorders. Typically, auscultation is practiced using a standard stethoscope by a healthcare professional to count respiration rate and listen for lung and heart function. However, using a stethoscope over a long period of time is impractical and inaccurate due primarily to human error. To more accurately count respiration rate, a technique called phonopneumography is used to record and analyze breath sounds measured using an acoustic sensor. Specifically, the acoustic sensor detects analog acoustic signals associated with respiration; these signals can then be digitized and analyzed using a computer algorithm to derive respiratory rate.

A number of issued U.S. Patents describe respiration rate calculated using phonopneumography. For example, U.S. Pat. Nos. 6,261,238 and 5,309,922 both describe an apparatus that includes conventional acoustic sensors and processing components that use this technique to determine respiration rate.

PTT, defined as the transit time for a pressure pulse launched by a heartbeat in a patient's arterial system, has been shown in a number of studies to correlate to both systolic and diastolic blood pressure. In these studies, PTT is typically measured with a conventional vital signs monitor that includes separate modules to determine both ECG and pulse oximetry. PTT is typically defined as the temporal difference between a portion of the time-dependent ECG waveform, which is typically measured with electrodes, and a portion of a time-dependent optical waveform (called a photoplethysmograph, or PPG), measured with a pulse oximeter.

Specifically, during a PTT measurement, multiple electrodes typically attach to a patient's chest to determine a time-dependent ECG component featuring a sharp spike called the R-wave of a 'QRS complex'. This feature indicates an initial depolarization of ventricles within the heart and, informally, marks the beginning of the heartbeat and a pressure pulse that follows. Pulse oximetry is typically measured with a bandage or clothespin-shaped sensor that attaches to a patient's finger, and includes optical systems operating in both the red and infrared spectral regions. A photodetector measures radiation emitted from the optical systems and transmitted through the patient's finger. Other body sites, e.g., the ear, forehead, and nose, can also be used in place of the finger. During a measurement, a microprocessor analyses both red and infrared radiation measured by the photodetector to determine the patient's blood oxygen saturation level and the PPG. Time-dependent features of the PPG indicate both pulse rate and a volumetric, optical absorbance change in an underlying artery (e.g., in the finger) caused by the propagating pressure pulse.

A number of issued U.S. Patents describe the relationship between PTT and blood pressure. For example, U.S. Pat. Nos. 5,316,008; 5,857,975; 5,865,755; and 5,649,543 each describe an apparatus that includes conventional sensors that measure an ECG and the PPG, which are then processed to determine PTT.

SUMMARY OF THE INVENTION

Embodiments described herein provide a body-worn vital signs monitor that measures respiratory rate and other vital signs using a small-scale acoustic sensor. The acoustic sensor is combined with and an ECG electrode in an adhesive patch sensor. The acoustic sensor measures respiration rate by recording sounds related to the patient's inspiration and expiration. The acoustic sensor is typically placed near the patient's trachea, but can also be placed on the middle right and left side of the chest, and the middle right and left side of the back. To measure blood pressure, the body-worn unit additionally performs a 'hybrid' PTT-based measurement that features both pressure-dependent and pressure-free measurements. In addition to blood pressure and respiratory rate, the vital sign monitor measures an optical plethysmograph or PPG waveform and ECG waveform, both of which can be processed to determine heart rate. Both the ECG and PPG waveforms can also be processed to determine respiratory rate as a backup method.

The vital sign monitor used to perform the respiratory rate measurement is typically a body-worn unit attached to either of the patient's upper arms. The body-worn unit includes a short-range wireless transmitter (e.g., a Bluetooth® transmitter) that wirelessly sends information to a handheld (or bedside) device that includes many features of a conventional personal digital assistant (PDA). The device includes, for example, a microprocessor that runs an icon-driven graphical user interface (GUI) on a color, liquid crystal display (LCD) attached to a touch panel. A user selects different measurement modes, such as continuous measurements in a hospital, one-time measurements at home or in a hospital, and 24-hour ambulatory modes, by tapping a stylus on an appropriate icon within the GUI. The device also includes several other hardware features commonly found in PDAs, such as short-range (e.g., Bluetooth® and WiFi®) and long-range (e.g., CDMA, GSM, IDEN) wireless modems, global positioning system, digital camera, and barcode scanner.

In general, in one aspect, the invention features a system configured to be worn on the body of a patient and includes a sensor assembly and a controller unit. The sensor assembly includes at least two electrodes, each configured to contact the patient's skin to detect separate electrical signals representing activity of the patient's heart; and an acoustic sensor configured to detect an acoustic signal from the patient's heart. The controller unit is configured to be worn on the patient's body, is configured to connect to the sensor assembly through a connector, and includes: an analog-signal processing circuit having a first amplifier configured to receive the electrical signals from the electrodes and generate an analog electrical waveform therefrom, and a second amplifier configured to receive the acoustic signal from the acoustic sensor and generate an analog acoustic waveform therefrom; analog-to-digital converter circuitry configured to receive the analog electrical waveform and generate a digital electrical waveform therefrom, and to receive the analog acoustic waveform and generate a digital acoustic waveform therefrom; and a processing circuit programmed to use the digital electrical waveform to determine a value for a vital sign for the patient, and to use the digital acoustic waveform to determine a respiratory rate for the patient.

In general, in another aspect, the invention features a system configured to be worn on the body of a patient and including a sensor assembly and a controller unit. The sensor assembly includes: at least two electrodes, each configured to contact the patient's skin to detect separate electrical signals representing activity of the patient's heart; and an acoustic sensor configured to detect an acoustic signal from the patient's heart. The controller unit is configured to be worn on the patient's body, is configured to connect to the sensor assembly through a connector, and includes: an analog-signal processing circuit having a first amplifier configured to receive the electrical signals from the electrodes and generate an analog electrical waveform therefrom, and a second amplifier configured to receive the acoustic signal from the acoustic sensor and generate an analog acoustic waveform therefrom; analog-to-digital converter circuitry configured to receive the analog electrical waveform and generate a digital electrical waveform therefrom, and to receive the analog acoustic waveform and generate a digital acoustic waveform therefrom; and a processing circuit programmed to use the digital electrical waveform to determine a first respiratory rate, and to use the digital acoustic waveform to determine a second respiratory rate, the processing circuit further programmed to analyze at least one of the digital electrical waveform and the digital acoustic waveform and, based on said analysis, select either the first respiratory rate or the second respiratory rate.

In general, in still another aspect, the invention features a system configured to be worn on the body of a patient and including: a sensor assembly and a controller unit. The sensor assembly includes: an optical sensor having a light source and a photodetector, and further configured to be proximal to the patient's skin to generate an optical signal representing a flow of blood within the patient; and an acoustic sensor configured to detect an acoustic signal from the patient's heart. The controller unit is configured to be worn on the patient's body, is configured to connect to the sensor assembly through a connector, and includes: an analog-signal processing circuit having a first amplifier configured to receive the optical signal from the photodiode and generate an analog optical waveform therefrom, and a second amplifier configured to receive the acoustic signal from the acoustic sensor and generate an analog acoustic waveform therefrom; analog-to-digital converter circuitry configured to receive the analog optical waveform and generate a digital optical waveform therefrom, and to receive the analog acoustic waveform and generate a digital acoustic waveform therefrom; and a processing circuit programmed to use the digital optical waveform to determine a first respiratory rate, and to use the digital acoustic waveform to determine a second respiratory rate, the processing circuit further programmed to analyze at least one of the digital optical waveform and the digital acoustic waveform and, based on said analysis, select either the first respiratory rate or the second respiratory rate.

At least some of the other embodiments include one or more of the following features. The sensor assembly also includes a substrate that supports the acoustic sensor and at least one of the at least two electrodes. The system further includes an optical sensor including a light source and a photodetector, and configured to be proximal to the patient's skin to generate an optical signal representing a flow of blood within the patient. The vital sign is blood pressure; the analog-signal processing circuit also includes a third amplifier configured to receive the optical signal from the photodiode and generate an analog optical waveform therefrom; the analog-to-digital converter circuitry is further configured to receive the analog optical waveform and generate a digital optical waveform therefrom, and the processing circuit is further programmed to use both the digital optical waveform and the digital electrical waveform to determine the value of said vital sign.

Also, at least some of the embodiments include one or more of the following features. The processing circuit is programmed to determine the respiratory rate from the digital acoustic waveform by filtering the digital acoustic waveform, e.g. by applying a bandpass filter or successively applying each of a plurality of bandpass filters. The plurality of bandpass filters includes a first bandpass filter and a second bandpass filter, wherein the first bandpass filter passes a first band of frequencies and the second bandpass filter passes a second band of frequencies that is different from the first band of frequencies. For example, the frequencies of the first band of frequencies are above the second band of frequencies. The frequencies of first band of frequencies are greater than 100 Hz. The frequencies of the second band of frequencies are less than 1 Hz.

Other embodiments include one or more of the following features. The system also includes a wireless transmitter and the processing circuit is further programmed to send said value for said vital sign and the respiratory rate to a remote device via the wireless transmitter. The system further includes a flexible armband connected to the controller unit and serving to attached the controller unit to the patient's arm during use. The processing circuit is further programmed to process the digital electrical waveform to determine a second respiratory rate, to analyze at least one of the digital electrical waveform and the digital acoustic waveform for unwanted noise and, based on said analysis, to select either the first-mentioned respiratory rate or the second respiratory rate. The sensor assembly includes an adhesive layer to attach the sensor assembly to the patient's body. The acoustic sensor includes a microphone.

Embodiments describe herein have a number of advantages. Using a comfortable body-worn unit, they provide a continuous measurement of respiratory function, blood pressure, heart rate, and other vital signs in, e.g., a hospital environment. Information is sent wirelessly from the body-worn unit to the bedside monitor, meaning the patient can move throughout the hospital without being encumbered by wires.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIGS. 1A and 1B show, respectively, schematic top and plan views of a patch sensor that attaches to a patient's chest to measure acoustic and electrical waveforms.

FIGS. 5A and 5B are semi-schematic views of the patch sensor of FIGS. 1A and 1B placed, respectively, on the front side and back side of a patient.

FIG. 7A is a graph of a time-dependent acoustic waveform, featuring both low and high-frequency components, similar to that shown in FIG. 2.

FIG. 7B is a graph of a frequency-dependent waveform representing the Fourier Transform of the acoustic waveform shown in FIG. 7A.

FIG. 7C is a graph of a fixed-frequency bandpass filter used to filter high-frequency components from the frequency-dependent waveform of FIG. 7B.

FIG. 7D is a graph of a filtered, frequency-dependent waveform that results when the frequency-dependent waveform of FIG. 7B is filtered with the fixed-frequency bandpass filter of FIG. 7C.

FIG. 7E is a graph of a time-dependent acoustic waveform featuring only a low-frequency, oscillating signal that results from the inverse Fourier Transform of the frequency-dependent waveform of FIG. 7D.

FIG. 7F is a graph of a time-dependent square wave featuring a 'pulse' corresponding to each oscillation of the time-dependent acoustic waveform of FIG. 7E.

FIGS. 8A and 8B are graphs of time-dependent ECG and PPG waveforms, each including a low-frequency envelope that represents an indirect measurement of a patient's respiration rate.

FIG. 8C is a graph of a time-dependent acoustic waveform, representing a direct measurement of a patient's respiration rate, which includes a period of disruption.

FIG. 8D is a graph of a time-dependent acoustic waveform which results by processing the time-dependent acoustic waveform in FIG. 8C with the algorithm illustrated schematically by FIGS. 7A-7F.

DETAILED DESCRIPTION

Figure 2:
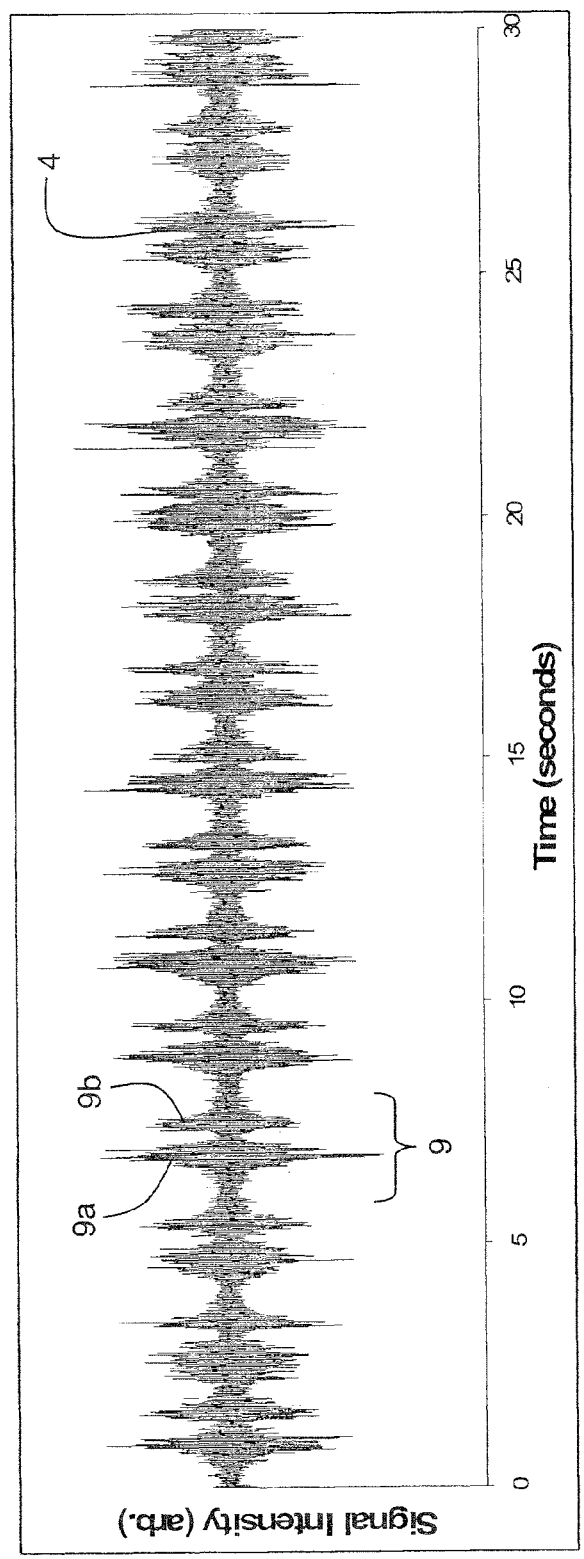
FIG. 2 shows a graph of a time-dependent acoustic waveform measured using the patch sensor of FIGS. 1A and 1B.

FIGS. 1A, 1B, and 2 show a patch sensor 42a that includes both an acoustic sensor 6 and electrode 7 for measuring respiration rate and electrical signals which can be used to determine other vital signs (e.g. heart rate). A foam backing 5 supports both components within the patch sensor 42a, which additionally includes an adhesive layer 8 on its opposing side. During operation, the adhesive layer secures the patch sensor 42a to the chest of a patient 40, preferably directly below their sternal notch. Both the sensor 6 and electrode 7 directly contact the patient's skin. The sensor 6 is preferably a small-scale microphone that senses 'sounds' associated with the patient's breathing, resulting in a time-dependent acoustic waveform 4, shown graphically in FIG. 2. The acoustic waveform 4 features a 'packet' 9 associated with each breath that includes first 9a and second 9b signals corresponding, respectively, to inspiration and expiration. Both the first 9a and second 9b signals are composed of a collection of acoustic frequencies, typically within 200-10,000 Hz, encompassed by an envelope with a width typically between 0.5 and 1 second. The features of the first 9a and second 9b signals depend on the patient's breathing rate. To determine respiratory rate, the acoustic sensor 6 detects an analog signal, which passes through a cable 51a to a body-worn unit described in detail below with reference to FIG. 4. The body-worn unit includes an analog-to-digital converter and microprocessor that, collectively, digitize and analyze the acoustic waveform 4 to determine the number of packets 9 during a short time period (e.g., 1 minute). This corresponds to the patient's breathing rate (typically expressed in breaths/minute).

Respiration rate does not depend on the individual acoustic sounds that make up the first 9a and second 9b signals within the packet; it only depends on the envelope that defines these signals. Thus, to simplify the calculation of respiration rate, the microprocessor executes computer code that calculates a filtered version of the time-dependent acoustic waveform 4 to determine a frequency-dependent waveform, as described in greater detail below. Relatively high frequencies within the frequency-dependent waveform, which are associated with the acoustic sounds, are then filtered using a low-pass mathematical filter. The microprocessor then transforms the waveform back to the time domain, passing only the relatively low frequencies. This process essentially reduces the acoustic waveform to a slowly varying, near-periodic waveform comprising low-frequency oscillations corresponding to the first and second signal (i.e., inspiration and expiration). The microprocessor then analyzes the resultant waveform by counting the oscillations or taking another Fourier transform to determine the respiration rate in the frequency domain.

In addition, the electrode 7 within the patch sensor 42a detects an analog electrical signal that passes through the same cable 51a to an amplifier/filter circuit within the body-worn unit. There, the electrical signal is combined with those measured by other electrodes placed on the patient's body to determine an ECG which is digitized and processed with, respectively, the analog-to-digital converter and microprocessor. Using a technique called the 'composite' measurement, the electrical waveform is combined with an optical waveform to determine the patient's blood pressure and heart rate. This process is described in detail in the following co-pending patent applications, the contents of which are incorporated herein by reference: VITAL SIGN MONITOR MEASURING BLOOD PRESSURE USING OPTICAL, ELECTRICAL, AND PRESSURE WAVEFORMS (U.S. Ser. No. 12/138,194; filed Jun. 12, 2008); and, VITAL SIGN MONITOR FOR CUFFLESSLY MEASURING BLOOD PRESSURE CORRECTED FOR VASCULAR INDEX (U.S. Ser. No. 12/138,199; filed Jun. 12, 2008).

Figure 3:
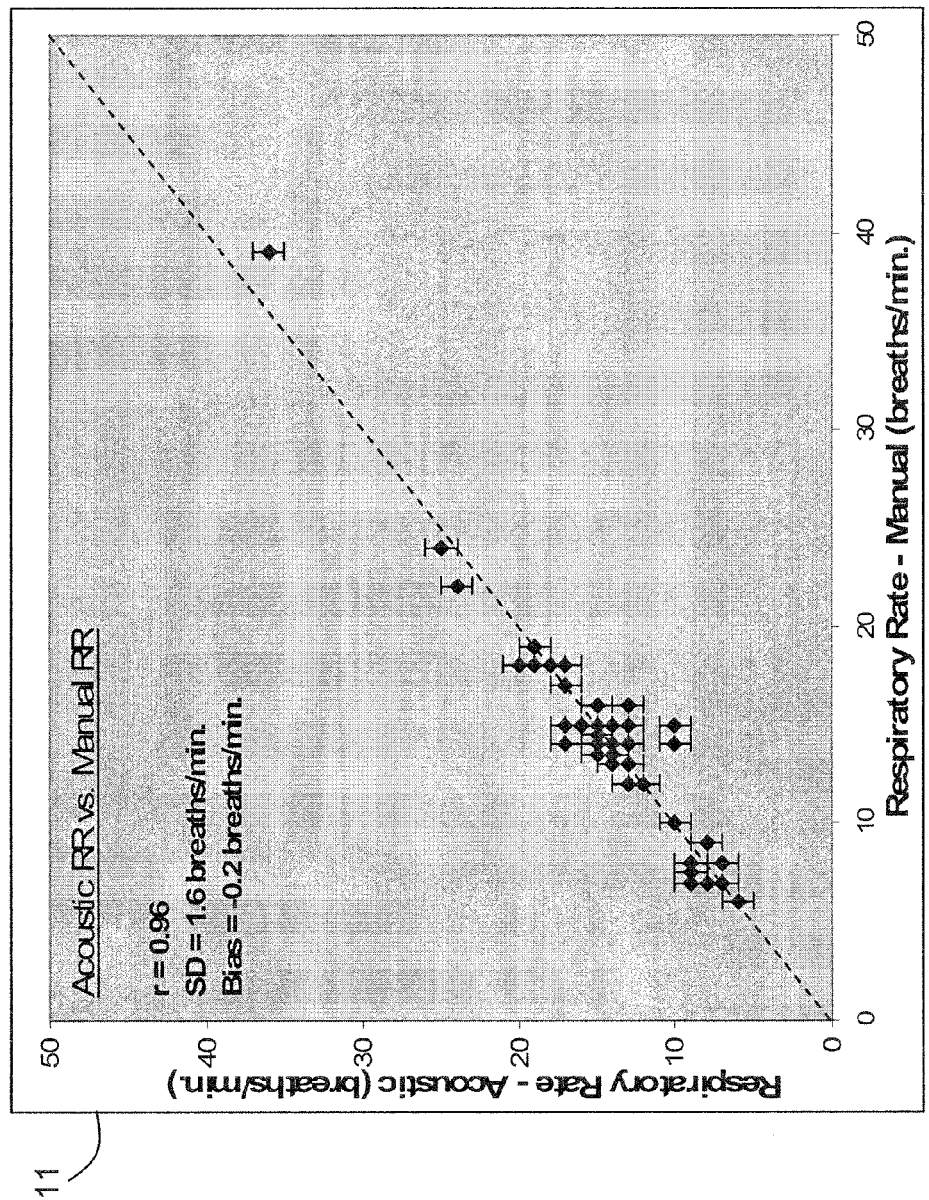
FIG. 3 shows a graph of respiratory rate measured with the patch sensor of FIGS. 1A and 1B correlated with respiratory rate measured manually by a medical professional.

Respiratory rate determined from the acoustic waveform 4 is typically accurate, as it represents a direct measurement of the patient's breathing rate. FIG. 3, for example, shows a graph 11 of respiratory rate determined with this method compared to that measured by manually counting the patient's breaths. The error in the manual method, shown by the error bars on each data point, is typically +/−1 breath/minute. On average, the bias for this correlation experiment is −0.2 breaths/minute, and the standard deviation of the differences between the acoustic and manual method is 1.6 breaths/minute. The correlation coefficient $r^2$ for the study was 0.96.

The acoustic waveform 4 is affected by other patient activities, such as talking and coughing. It can also include sounds associated with the closing of the patient's heart valves (i.e., closing of the mitral and aortic valve, which results in the characteristic 'lub' and 'dub' sounds associated with a heartbeat). Each of these activities can result in features in the acoustic waveform 4 that are not associated with breathing, and can thus reduce the accuracy of the measurement. The microprocessor analyzes the acoustic waveform and determines if the patient is coughing or talking, as these sounds are typically non-periodic and have higher amplitudes compared to sounds associated with inspiration and expiration. Following this analysis the microprocessor determines that analysis of the acoustic waveform will not result in an accurate respiration rate, and thus determines this property from either the optical or electrical waveform.

Specifically, the envelope of both these signals is known to be modulated by respiration rate, as is described in the attached references, the contents of which are incorporated herein by reference: 1) 'A Fully Automated Algorithm for the Determination of Respiratory Rate from the Photoplethysmogram', *Journal of Clinical Monitoring and Computing* 20: 33-36 (2006); 2) 'Photoplethysmographic Measurement of Heart and Respiratory Rates Using Digital Filters', *IEEE* 1/93: 1006-1007 (1993); and, 3) 'Validation of an ECG-Derived Respiration monitoring Method', *Computers in Cardiology* 30: 613-616 (2003). Analyzing the envelope (using, e.g., Fourier analysis) of an ECG or PPG yields an indirect measurement of respiratory rate. Once the microprocessor determines the coughing or talking has subsided, it returns to a direct measurement of respiratory rate from the acoustic waveform.

In the described embodiment, the acoustic sensor is a small-scale, solid state microphone, such as that manufactured by Free Scale Semiconductors, Part Number MPXM2051GS or a microphone manufactured by Panasonic, Part Numbers WM-55A103 and WM-63GC/63GN. Typically, the acoustic waveform from this sensor is sampled between ~100 Hz and ~1000 Hz, and is digitized with 10-16-bit resolution.

Figure 4:
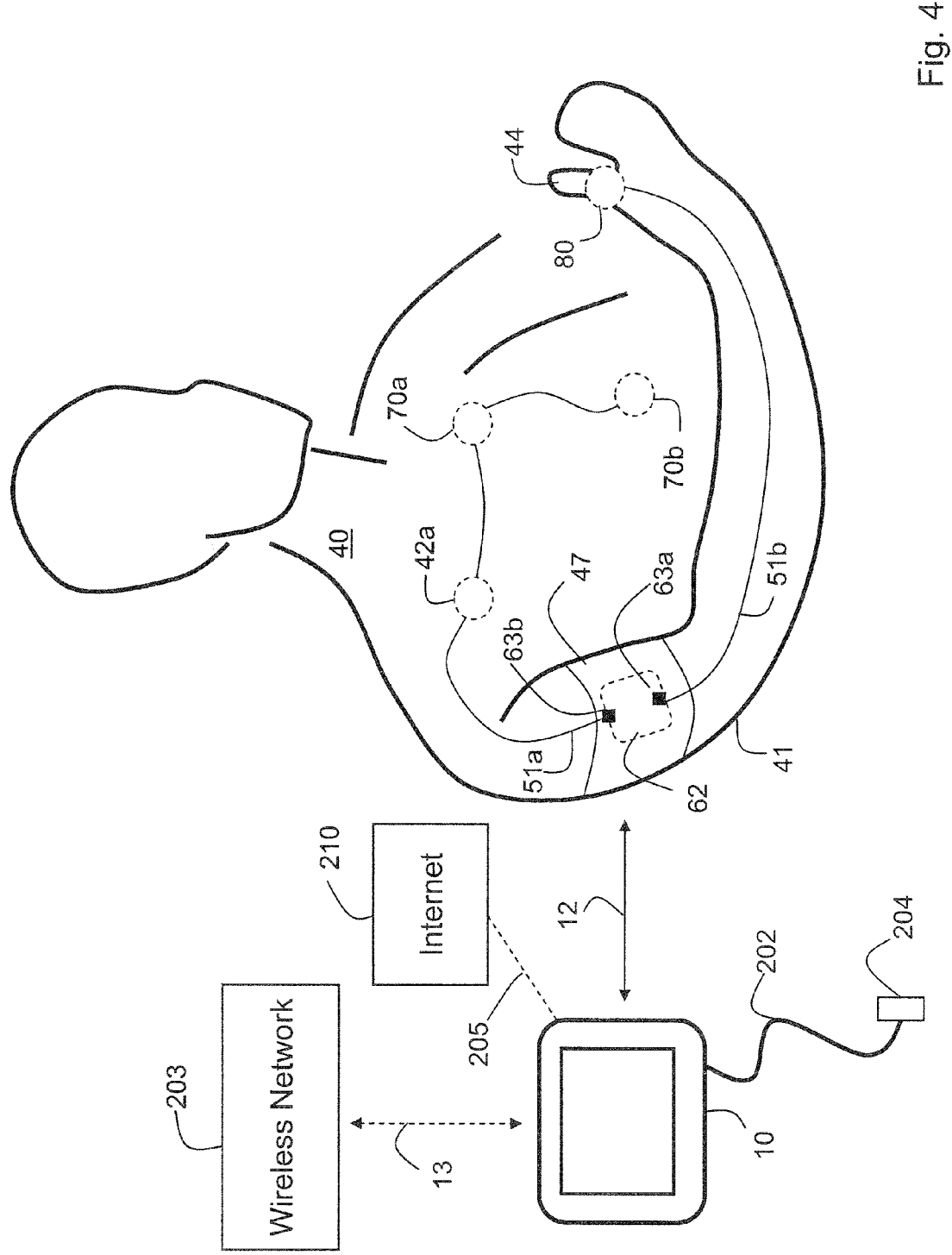
FIG. 4 is a schematic view of a body-won unit attached to the patch sensor of FIGS. 1A and 1B that measures blood pressure, respiration rate, and other vital signs, and communicates wirelessly with a bedside monitor.

FIG. 4 shows a system that measures respiratory rate along with a PTT-based blood pressure value from a patient 40. The blood pressure measurement used by this device is preferably the composite measurement, described above. Prior to the measurement, a medical professional or patient places a body-worn unit 47 on the patient's upper arm 41 above their brachial artery. The body-worn unit 47 includes an optical sensor 80 featuring two green LEDs and a photodetector within the optical module and two adhesive ECG electrodes 70a, 70b that both attach to the patient's chest. The optical sensor 80 connects to the body-worn unit 47 through a removable second cable 51b, and attaches to the patient's thumb using an overlying adhesive patch (not shown in the figure). A flexible strap secures the body-worn unit 47 to the patient's arm 57. The optical sensor 80 is disposed proximal to the patient's 'princeps pollics' artery 44, which is located near the thumb. The ECG electrodes 70a, 70b, and the patch 42a adhere to the patient's chest in a standard Einthoven's triangle configuration, and connect to the body-worn unit 47 though a first cable 51a. Placement of the optical sensor 80 on the patient's thumb is further described detail in the following co-pending patent application, the contents of which are incorporated herein by reference: SYSTEM FOR MEASURING BLOOD PRESSURE FROM A PATIENT (U.S. Ser. No. 61/073,681; filed Jun. 18, 2008).

The patch sensor 42a attaches to the patient's chest and connects to the armband 47 through a first cable 51a. Alternatively, the patch sensor 42a attaches to a nearby location, e.g., the patient's shoulder or back. To measure temperature, a temperature probe (not shown) may be placed on the upper arm, axilla, ear, or within the patch sensor 42a. The first 51a cable connects through a stereo-jack connector 63a and the second cable 51b connects through a DB-9 connector 63b to an electronics module 62 which is part of body-worn unit 47. This allows these cables 51a, 51b to be easily detached.

For the composite blood pressure measurement, the body-worn unit's flexible strap includes a pneumatic bladder that connects through a manifold or tubing to a pump system that includes a mechanical pump, solenoid relief valve, and pressure sensor within the electronics module. A conventional cuff may be used in place of the pneumatic bladder. During operation, the microprocessor sends a signal to an electrical switch (e.g., a field effect transistor) that activates the mechanical pump within the pump system, which in turn fills up the bladder with air, and then closes the relief valve. The signal, for example, can be a constant signal, or a time-dependent electrical pulse having an adjustable width. The activated pump applies pressure to the bladder, which is measured by the sensor within the pump system. The bladder applies pressure to the underlying brachial artery according to a pressure waveform. The optical sensor measures an optical waveform from the brachial artery that is modulated by the applied pressure. The microprocessor in the body-worn sensor then analyzes the optical waveform according to the algorithm in the above-mentioned patent application to determine the patient's blood pressure.

A number of other methods can be used to calculate blood pressure from PTT measured as described above. Such methods are described in the following co-pending patent applications, the contents of which are incorporated herein by reference: 1) CUFFLESS BLOOD-PRESSURE MONITOR AND ACCOMPANYING WIRELESS, INTERNET-BASED SYSTEM (U.S. Ser. No. 10/709,015; filed Apr. 7, 2004); 2) CUFFLESS SYSTEM FOR MEASURING BLOOD PRESSURE (U.S. Ser. No. 10/709,014; filed Apr. 7, 2004); 3) CUFFLESS BLOOD PRESSURE MONITOR AND ACCOMPANYING WEB SERVICES INTERFACE (U.S. Ser. No. 10/810,237; filed Mar. 26, 2004); 4) VITAL SIGN MONITOR FOR ATHLETIC APPLICATIONS (U.S. Ser. No.; filed Sep. 13, 2004); 5) CUFFLESS BLOOD PRESSURE MONITOR AND ACCOMPANYING WIRELESS MOBILE DEVICE (U.S. Ser. No. 10/967,511; filed Oct. 18, 2004); 6) BLOOD PRESSURE MONITORING DEVICE FEATURING A CALIBRATION-BASED ANALYSIS (U.S. Ser. No. 10/967,610; filed Oct. 18, 2004); 7) PERSONAL COMPUTER-BASED VITAL SIGN MONITOR (U.S. Ser. No. 10/906,342; filed Feb. 15, 2005); 8) PATCH SENSOR FOR MEASURING BLOOD PRESSURE WITHOUT A CUFF (U.S. Ser. No. 10/906,315; filed Feb. 14, 2005); 9) PATCH SENSOR FOR MEASURING VITAL SIGNS (U.S. Ser. No. 11/160,957; filed Jul. 18, 2005); 10) WIRELESS, INTERNET-BASED SYSTEM FOR MEASURING VITAL SIGNS FROM A PLURALITY OF PATIENTS IN A HOSPITAL OR MEDICAL CLINIC (U.S. Ser. No. 11/162,719; filed Sep. 9, 2005); 11) HAND-HELD MONITOR FOR MEASURING VITAL SIGNS (U.S. Ser. No. 11/162,742; filed Sep. 21, 2005); 12) CHEST STRAP FOR MEASURING VITAL SIGNS (U.S. Ser. No. 11/306,243; filed Dec. 20, 2005); 13) SYSTEM FOR MEASURING VITAL SIGNS USING AN OPTICAL MODULE FEATURING A GREEN LIGHT SOURCE (U.S. Ser. No. 11/307,375; filed Feb. 3, 2006); 14) BILATERAL DEVICE, SYSTEM AND METHOD FOR MONITORING VITAL SIGNS (U.S. Ser. No. 11/420,281; filed May 25, 2006); 15) SYSTEM FOR MEASURING VITAL SIGNS USING BILATERAL PULSE TRANSIT TIME (U.S. Ser. No. 11/420,652; filed May 26, 2006); 16) BLOOD PRESSURE MONITOR (U.S. Ser. No. 11/530,076; filed Sep. 8, 2006); 17) TWO-PART PATCH SENSOR FOR MONITORING VITAL SIGNS (U.S. Ser. No. 11/558,538; filed Nov. 10, 2006); and, 18) MONITOR FOR MEASURING VITAL SIGNS AND RENDERING VIDEO IMAGES (U.S. Ser. No. 11/682,177; filed Mar. 5, 2007).

During a blood pressure measurement, the patient's heart generates electrical impulses that pass through the body near the speed of light. These impulses stimulate each heart beat, which in turn generates a pressure wave that propagates through the patient's vasculature at a significantly slower speed. Immediately after the heartbeat, the pressure wave leaves the aorta, passes through the subclavian artery, to the brachial artery, and from there through the radial artery to smaller digital arteries in the patient's fingers. The two ECG electrodes 70a, 70b in the body-worn unit 47 and the electrode in the patch sensor 42a detect separate unique electrical signals which pass to an differential amplifier/filter circuit within the electronics module 62. There, the signals are processed using the differential amplifier/filter circuit to determine an analog electrical signal, which is digitized with an analog-to-digital converter to form the electrical waveform and then stored in memory. Using a reflection-mode geometry, the optical sensor 80 attached to the body-worn unit 47 measures an optical waveform from either the patient's brachial and radial arteries. A second optical sensor, not shown in the figure, can be used to measure a second optical waveform from one of these arteries. These signals are amplified using second and third amplifier/filter circuits and digitized with second and third channels within the analog-to-digital converter in the electronics module 62. Each optical waveform features a time-dependent 'pulse' corresponding to each heartbeat that represents a volumetric absorbance change in an underlying artery caused by the propagating pressure pulse.

The above-described system can be used in a number of different settings, including both the home and hospital. A patient 40 in a hospital, for example, can continuously wear the body-worn unit 47 over a time period ranging from minutes to several days. During this period, the body-worn unit 47 is powered by a rechargeable battery, and continuously measures blood pressure along with other vital signs. At a predetermined interval (typically, every few minutes) the body-worn unit transmits this information through a short-range wireless interface 12 (e.g., a Bluetooth® interface) to the bedside device 10. The device 10 can easily seat by the patient's bed to be easily seen by the patient or caregiver and additionally includes an AC adaptor 202 that plugs into a wall outlet 204 and continuously charges the device's battery as well as a spare for the armband 47. The device 10 is highly portable and can communicate with a nationwide wireless network 203 (e.g., Sprint) through a long-range wireless interface 13 (e.g., a CDMA modem), or with the Internet 210 through a wired or wireless (e.g., 802.11) interface 205.

The optical modules within the optical sensor 80 typically include an LED operating near 570 nm, a photodetector, and an amplifier. This wavelength is selected because it is particularly sensitive to volumetric absorbance changes in an underlying artery for a wide variety of skin types when deployed in a reflection-mode geometry, as described in the following co-pending patent application, the entire contents of which are incorporated herein by reference: SYSTEM FOR MEASURING VITAL SIGNS USING AN OPTICAL MODULE FEATURING A GREEN LIGHT SOURCE (U.S. Ser. No. 11/307,375; filed Feb. 3, 2006). The optical sensor detects reflected radiation, which is further processed with a second amplifier/filter circuit within the body sensor. This results in the optical waveform, which, as described above, includes a series of pulses, each corresponding to an individual heartbeat. As indicated above, a second optical sensor can also be used to measure a second optical waveform from one of these arteries. The second optical sensor can include LEDs operating near 650 nm and 950 nm in order to make a pulse oximetry measurement.

FIGS. 5A and 5B show, respectively, front and back views of a patient 40', 40" and locations where the patch sensor 42a can be located to measure acoustic and electrical waveforms. As shown in FIG. 5A, the patch sensor 42a typically adheres to the chest of the patient 40', proximal to the heart. However, to obtain stronger tracheal breath sounds, the sensor can be located just above the sternal notch 105. Alternate locations include the patient's middle right 106 and left sides 107 of the chest, and middle right 109 and left side 109 of the back. In these locations the sensor measures inhalational and exhalation as the patient's lungs expand and contract with each breath.

Figure 6A:
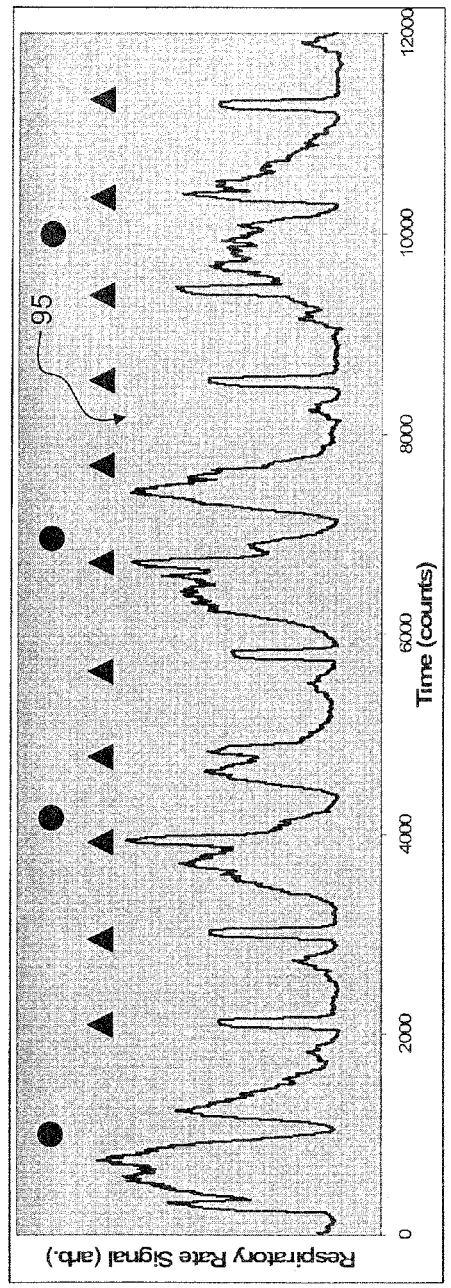
FIGS. 6A and 6B show graphs of unfiltered and filtered acoustic waveforms processed with a digital filtering algorithm operating on the body-worn sensor.
Figure 6B:
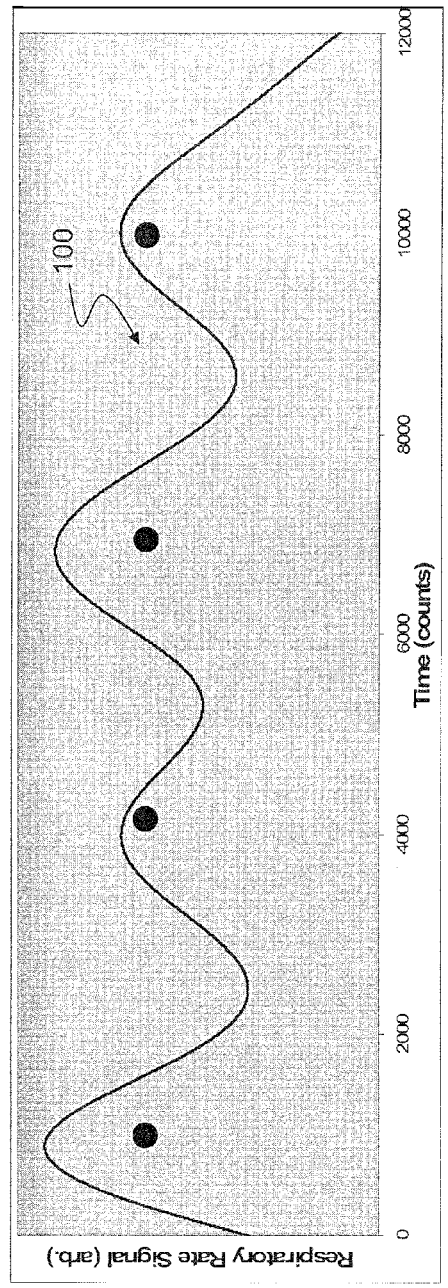

In some cases, the previously mentioned filtering steps are used to iteratively process the acoustic waveform so that high-frequency components are completely removed, leaving only low-frequency components which can be easily analyzed with an algorithm to determine respiratory rate. The iterative process may include two or more filtering steps. For example, FIG. 6A shows a graph of a time-dependent acoustic waveform 95 after it has been filtered once with a software-based digital filter. The waveform 95 includes two primary features: 1) those due to sounds associated with respiration (i.e. inspiration and expiration), as indicated by the solid circles; and 2) those due to sounds associating with the closing of valves in the heart (i.e., mitral and aortic valves), as indicated by the solid triangles. In an unfiltered waveform, both these features are composed primarily of high-frequency acoustic signals that are difficult to process with a computer algorithm (e.g., a conventional 'peak picking' algorithm). The waveform 95 in FIG. 6A has been filtered by a first bandpass filter that passes frequency components between 300-1100 Hz. This filtering leaves a waveform 95 that lacks the very high-frequency components associated with the actual acoustic processes that make up the heart and lung sounds, but still includes the slightly lower frequency components that, collectively, describe a waveform 95 that represents these sounds. Processing this waveform 95 to exclusively determine respiratory rate is difficult, however, because of the jagged edges associated with the respiratory signals (circles), and additionally because of sharp edges associated with heart rate signals (triangles). To mitigate this problem, the waveform 95 in FIG. 6A can be filtered with a second bandpass filter that only passes frequency components between 0.1-0.5 Hz. This filtering removes high-frequency components associated with the heart rate signal and the jagged edges of the respiratory rate signal. As shown in FIG. 6B, this leaves a waveform 100 featuring a smooth, low-frequency oscillation that can be easily processed with a computer algorithm to determine respiratory rate. For this particular data, a two-stage filtering approach is preferable to a one-stage filtering approach (using a bandpass filter between 0.1 and 1 Hz), as this process may distort the acoustic waveform to a point where it is difficult to accurately determine respiratory rate.

FIGS. 7A-7F show graphs resulting from the various steps of a software-based algorithm used to digitally filter an acoustic waveform and, in response, calculate respiratory rate. FIG. 7A shows a graph of an unfiltered, time-dependent acoustic waveform 110 measured with the patch sensor similar to that shown in FIGS. 1A and 1B. The waveform 110 features both low and high-frequency components, and is similar to that shown in FIG. 2. Processing the waveform 110 with a fast Fourier Transform (FFT) algorithm yields a frequency-dependent waveform 111 shown in FIG. 7B that features 4 distinct frequency components. The first ($f_1$) is a low-frequency component (~0.1-0.2 Hz) due to inspiration and expiration events associated with respiration rate. The second ($f_2$) is associated with heart rate, and is typically of slightly higher frequency (~0.5-2.0 Hz). The third ($f_3$) is a well-defined frequency (60 Hz) associated with noise related to room lights, electrical equipment, etc. that may be proximal to the patient. The fourth ($f_4$) is a high-frequency component associated with the actual acoustic processes that compose the heart and lung sounds. (Note that the frequency-dependent waveform 111 is not to scale.)

A digital bandpass filter, shown schematically by the waveform 112 in FIG. 7C, is then applied to the frequency-dependent waveform 111 of FIG. 7B. This passes the first frequency component $f_1$, without any attenuation. In a preferred embodiment, the FFT-based filtering algorithm is a digital bandpass filter, implemented as a Finite Impulse Response Windowed-Sine Filter (FIR-WS filter). Typically, as described with reference to FIGS. 6A and 6B, this initial filter has a pass band between 300 Hz and to 1.1 kHz (e.g. frequencies that are greater than 100 Hz), and rejects any frequencies outside of this range. In general, the cutoff frequencies are chosen such that external noise sources are removed, but the fundamental frequencies describing inspiration and expiration are unaltered. Typically the initial filter reduces, but does not completely eliminate, the extraneous frequencies. FIG. 7D shows a frequency-dependent waveform 113 that indicates how the frequency associated with respiration rate ($f_1$) is essentially unaltered by the digital bandpass filter of FIG. 7C, but the residual frequency components ($f_2$-$f_4$) remain in the waveform even after the initial filtering process. The relative amplitudes of these components will depend on the boundaries of the bandpass filter.

FIG. 7E is a graph of a time-dependent acoustic waveform 114 featuring primarily a low-frequency, oscillating signal that results from the inverse Fourier Transform of the frequency-dependent waveform 113 of FIG. 7D. As described with reference to FIG. 6B, the waveform 114 may include temporal components resulting from the residual frequency components ($f_2$-$f_4$) that pass through the first digital bandpass filter. In this case, the filtering process is repeated, and the bounds of the digital bandpass filter shown in FIG. 7C are typically between 0.1 and 0.5 Hz (e.g. frequencies that are less than 1 Hz). This process can be iteratively repeated until only the frequency component $f_1$, associated with respiratory rate remains. The filtering iteration, for example, can be triggered when the inverse Fourier Transform results in a waveform that has a peak with non-zero amplitude outside of 0.1-0.2 Hz.

The FFT-based digital filtering algorithms described above are well known in signal processing, and are described, for example, in 'Numerical Recipes in C' (1988), published by Cambridge University Press, the contents of which are incorporated by reference.

Multiple filtering iterations eventually yield a time-dependent waveform 114, shown in FIG. 7D, which features a series of smooth oscillations, each corresponding to a single inspiration/expiration event. These oscillations can be processed with a conventional peak-detecting algorithm (e.g. an algorithm that analyzes the first and/or second derivative of the oscillations). Following processing, this algorithm generates a train 115 of square-wave pulses, shown in FIG. 7F, with each pulse corresponding to a single oscillation in FIG. 7E. The pulses in the train 115 can then be easily counted by an algorithm to determine respiratory rate.

Inspiration and expiration directly impact the acoustic waveform, and thus the above-described method represents a direct determination of respiratory rate. In contrast, respiratory rate has an indirect impact on both ECG and PPG waveforms, which are primarily used to determine heart rate, pulse oximetry and blood pressure using the above-referenced composite technique. Specifically, inspiration and expiration affect both the capacitance of a patient's chest and the degree of oxygenation of their blood. The change in capacitance modulates the time-dependent amplitude of the ECG waveform, which in turn modulates the electrical signal monitored by the chest-worn electrodes. Similarly, a respiration rate-induced change in blood oxygenation modulates the time-dependent amplitude of the PPG waveform, which is monitored by an optical sensor, typically placed on the patient's finger or earlobe. Respiration rate can therefore be determined indirectly by measuring and processing a time-dependent change in the amplitudes of these waveforms (i.e. the 'envelopes' of these waveforms). The envelopes can be extracted from the waveforms using multiple, established techniques, including Fourier analysis (similar to the techniques described above), wavelet transformations, fitting, or simply by monitoring peak values of pulses in the ECG and PPG waveforms, and then drawing a smooth, interpolated line through these peak values. In general, a direct measurement of any property is typically more accurate, and thus preferable, to an indirect one. Direct measurement of respiration rate from the acoustic waveform is thus typically preferable to an indirect measurement of this property from the ECG or PPG waveforms.

In an embodiment, the patch sensor described above is used to determine both acoustic and ECG waveforms. In still another embodiment, an optical sensor, operating in either transmission or reflection-mode geometry and described in the above-referenced patent applications, can determine a PPG waveform. An algorithm, operating on the body-worn unit, then determines respiratory rate directly from the acoustic waveform. If the acoustic waveform is corrupted by noise sources (caused, e.g., by the patient coughing, snoring, or talking), the algorithm switches to determine respiration rate indirectly from the ECG waveform, or alternatively the PPG waveform. These waveforms are relatively immune to the above-mentioned noise sources.

FIGS. 8A-8D illustrate this two-part approach for determining respiration rate with both direct and indirect methods. Specifically, FIGS. 8A and 8B show, respectively, graphs of an ECG waveform 360 and PPG waveform 361. The ECG waveform 360 in FIG. 8A features a series of pulses 371 having amplitudes which are modulated according to an oscillating envelope 355. Each pulse corresponds to an individual heartbeat. As described above, the amplitudes of the pulses 371 are modulated because the patient's breathing pattern affects the capacitance of their chest. Similarly, the PPG waveform 361 in FIG. 8B also includes a series of pulses 372, measured by an optical sensor, that are characterized by a similar envelope 356. The envelopes 355, 356 of the ECG and PPG waveforms can be determined as described above; both can be processed to determine an indirect measurement of respiratory rate.

FIG. 8C shows an acoustic waveform 362 similar to that shown in FIGS. 2 and 7A. This waveform 362 is processed according to an algorithm using a two-step digital bandpass filter, shown schematically by FIGS. 7A-7F, to determine the smoothed waveform 363 in FIG. 8D. The waveform 362 in FIG. 8C features a period of distortion 357 caused by an acoustic process, unrelated to respiration, that could be caused by the patient coughing, sneezing, belching, talking. Alternatively the acoustic process could be related to a direct disturbance of the acoustic sensor position (e.g., a patient's shirt rubbing against the back of the sensor). The digital filtering process described above does not remove the period of distortion 357, and thus the smoothed waveform 363 includes a similar artifact. Such an artifact affects the accuracy of respiratory rate determined from this waveform. Note that the ECG 360 and PPG 361 waveforms are unaffected by the period of distortion 357; in this case, therefore, the accuracy of respiratory rate determined from these waveforms is not compromised.

During a measurement, a microprocessor analyzes the smoothed acoustic 363, ECG 361, and PPG 360 waveforms.

Software running on the microprocessor determines if a period of distortion 359 is present on the smoothed acoustic waveform 363; such a distortion affects the accuracy of the measured respiratory rate. The software, for example, can identify the period of distortion 359 by analyzing its time-dependent duration, amplitude, and shape. If a period of distortion 359 is determined, the software determines respiratory rate from the envelopes 355, 356 characterizing the ECG and PPG waveforms. These envelopes 355, 356 can be analyzed independently or collectively.

Still other embodiments are within the following claims.

What is claimed is:

1. A system configured to be worn on the body of a patient and comprising:
   a sensor array comprising
      a first ECG electrode configured to contact the patient's skin to detect a first electrical signal representing activity of the patient's heart;
      a second ECG electrode configured to contact the patient's skin to detect a second electrical signal representing activity of the patient's heart;
      an adhesive patch sensor comprising a third ECG electrode and an acoustic sensor configured to detect a third electric signal representing activity of the patient's heart and an acoustic signal for the patient's heart;
      a first cable configured to operably connect the first ECG electrode, second ECG electrode, and adhesive patch sensor to a controller unit via a first terminal connector;
   an optical sensor comprising
      a light source and a photodetector configured to be proximal to the patient's skin to generate an optical signal representing a flow of blood within the patient; and
      a second cable configured to operably connect the optical sensor to the controller unit via a second terminal connector;
   the controller unit, wherein the controller unit is configured to be worn on the patient's body, and further configured to operably connect to the first ECG electrode, second ECG electrode, and adhesive patch sensor by receiving the first terminal connector and to the optical sensor by receiving the second terminal connector, the controller unit comprising:
      an analog-signal processing circuit comprising a first amplifier configured to receive the electrical signals from the first ECG electrode, second ECG electrode, and third ECG electrode and generate an analog electrical waveform therefrom, a second amplifier configured to receive the acoustic signal from the acoustic sensor and generate an analog acoustic waveform therefrom, and a third amplifier configured to receive the optical signal from the photodiode and generate an analog optical waveform therefrom;
      analog-to-digital converter circuitry configured to receive the analog electrical waveform and generate a digital electrical waveform therefrom, to receive the analog acoustic waveform and generate a digital acoustic waveform therefrom, and to receive the analog optical waveform and generate a digital optical waveform therefrom; and
      a processing circuit programmed to use the digital electrical waveform to determine a value for a vital sign for the patient, to use the digital acoustic waveform to determine a first respiratory rate, and to use the digital optical waveform to determine a second respiratory rate, the processing circuit further programmed to analyze at least one of the digital acoustic waveform and the digital optical waveform and, based on said analysis, select either the first respiratory rate or the second respiratory rate to determine a respiratory rate for the patient.

2. The system of claim 1, wherein said vital sign is blood pressure, and wherein the processing circuit is further programmed to use both the digital optical waveform and the digital electrical waveform to determine the value of said vital sign.

3. The system of claim 1, wherein the processing circuit is programmed to determine the first respiratory rate from the digital acoustic waveform by filtering the digital acoustic waveform.

4. The system of claim 3, wherein the filtering involves applying a bandpass filter.

5. The system of claim 3, wherein the filtering involves successively applying each of the plurality of bandpass filters.

6. The system of claim 5, wherein the plurality of bandpass filters comprises a first bandpass filter and a second bandpass filter, wherein the first bandpass filter passes a first band of frequencies and the second bandpass filter passes a second band of frequencies that is different from the first band of frequencies.

7. The system of claim 6, wherein the frequencies of the first band of frequencies are above the second band of frequencies.

8. The system of claim 6, wherein the frequencies of first band of frequencies are greater than 100 Hz.

9. The system of claim 6, wherein the frequencies of the second band of frequencies are less than 1 Hz.

10. The system of claim 1, further comprising a wireless transmitter and wherein the processing circuit is further programmed to send said value for said vital sign and the respiratory rate to a remote device via the wireless transmitter.

11. The system of claim 1, further comprising a flexible armband connected to the controller unit and serving to attach the controller unit to the patient's arm during use.

12. The system of claim 1, wherein the acoustic sensor comprises a microphone.

13. A system configured to be worn on the body of a patient and comprising: a sensor assembly comprising:
   a sensor array comprising
      a first ECG electrode configured to contact the patient's skin to detect a first electrical signals representing activity of the patient's heart;
      a second ECG electrode configured to contact the patient's skin to detect a second electrical signal representing activity of the patient's heart;
      an adhesive patch sensor comprising a third ECG electrode and an acoustic sensor configured to detect a third electric signal representing activity of the patient's heart and an acoustic signal for the patient's heart;
      a first cable configured to operably connect the first ECG electrode, second ECG electrode, and adhesive patch sensor to a controller unit via a first terminal connector;
   the controller unit, wherein the controller unit is configured to be worn on the patient's body, and further configured to operably connect to the first ECG electrode, second ECG electrode, and adhesive patch sensor by receiving the first terminal connector, the controller unit comprising:
      an analog-signal processing circuit comprising a first amplifier configured to receive the electrical signals from the first ECG electrode, second ECG electrode, and third ECG electrode and generate an analog electrical waveform therefrom, and a second amplifier configured to receive the acoustic signal from the acoustic sensor and generate an analog acoustic waveform therefrom;

analog-to-digital converter circuitry configured to receive the analog electrical waveform and generate a digital electrical waveform therefrom, and to receive the analog acoustic waveform and generate a digital acoustic waveform therefrom; and a processing circuit programmed to use the digital electrical waveform to determine a first respiratory rate, and to use the digital acoustic waveform to determine a second respiratory rate, the processing circuit further programmed to analyze at least one of the digital electrical waveform and the digital acoustic waveform and, based on said analysis, select either the first respiratory rate or the second respiratory rate to determine a respiratory rate for the patient.

14. The system of claim 13, wherein the processing circuit is programmed to determine the second respiratory rate form the digital acoustic waveform by filtering the digital acoustic waveform.

15. The system of claim 14, wherein the filtering involves applying a bandpass filter.

16. The system of claim 14, wherein the filtering involves successively applying each of a plurality of bandpass filters.

17. The system of claim 16, wherein the plurality of bandpass filters comprises a first bandpass filter and a second bandpass filter, wherein the first bandpass filter passes a first band of frequencies and the second bandpass filter passes a second band of frequencies that is different from the first band of frequencies.

18. The system of claim 17, wherein all the frequencies of the first band of frequencies are above the second band of frequencies.

19. The system of claim 17, wherein all the frequencies of the first band of frequencies are greater than 100 Hz.

20. The system of claim 17, wherein all the frequencies of the second band of frequencies are less than 1 Hz.

* * * * *